United States Patent [19]
Markowitz et al.

[11] Patent Number: 5,683,430
[45] Date of Patent: Nov. 4, 1997

[54] STATUS MONITOR FOR ANOMALY DETECTION IN IMPLANTED DEVICES AND METHOD

[75] Inventors: Raymond S. Markowitz, Elkins Park; Xiaoguang G. Sun, King of Prussia, both of Pa.

[73] Assignee: AEL Industries, Inc., Lansdale, Pa.

[21] Appl. No.: 559,101

[22] Filed: Nov. 16, 1995

[51] Int. Cl.$^6$ .................................................. A61N 1/37
[52] U.S. Cl. ................................................... 607/27
[58] Field of Search ........................ 607/27, 28; 128/903

[56] References Cited

U.S. PATENT DOCUMENTS

| | | | |
|---|---|---|---|
| 3,417,398 | 12/1968 | Lewis et al. | 332/57 |
| 3,618,615 | 11/1971 | Greatbatch . | |
| 3,830,242 | 8/1974 | Greatbatch . | |
| 4,142,533 | 3/1979 | Brownlee et al. . | |
| 4,220,156 | 9/1980 | Schulman et al. . | |
| 4,281,664 | 8/1981 | Duggan | 128/696 |
| 4,527,567 | 7/1985 | Fischler et al. . | |
| 4,944,299 | 7/1990 | Silvian . | |
| 5,233,985 | 8/1993 | Hudrlik | 607/27 |
| 5,233,986 | 8/1993 | Robson | 607/4 |
| 5,411,536 | 5/1995 | Armstrong | 607/32 |
| 5,423,871 | 6/1995 | Hoegnelid et al. | 607/28 |

*Primary Examiner*—Scott M. Getzow
*Attorney, Agent, or Firm*—Seidel, Gonda Lavorgna & Monaco, PC

[57] ABSTRACT

A status monitoring system for evaluating the condition of an electrode implanted in the body of a mammal. The system comprises a modulator for modulating interrogation signals on an electrode of an implanted device, and a monitor for analyzing modulated interrogation signals being reflected by the electrode. The monitor comprises a transmitter for transmitting interrogation signals, a receiver for receiving and processing the signals reflected by the electrode, and a microprocessor for controlling the transmitter and the receiver. The microprocessor producing electrode condition data from the signals processed by the receiver. The invention further comprises a communication system in communication with the monitoring device for transmitting the electrode condition data to a remote location. The interrogation signals are transmitted by the transmitter onto the electrode. The interrogation signals are modulated on the electrode by combining with a modulation signal generated by the modulator. The modulator is activated by the interrogation signals. The modulated interrogation signals are reflected by the electrode and received by the receiver. The receiver receiving and processing the received signal into a form usable by the microprocessor, the microprocessor producing therefrom the electrode condition data.

11 Claims, 3 Drawing Sheets

STATUS MONITOR FOR ANOMALY DETECTION IN IMPLANTED DEVICES AND METHOD

BACKGROUND OF THE INVENTION

This invention relates to the monitoring and evaluation of an electrode or wire lead associated with implanted medical devices such as pacemakers.

Implanted artificial devices such as pacemakers, bladder control devices, and internal medication dispensers and sensors are widely used in the medical treatment of both human beings and animals. Many of these implanted devices have electrodes that are placed in direct contact with vital organs or tissue. These electrodes are essential to the operation of the implanted device because they are used to sense a biological function or condition or used to administer some type of stimulation.

All implanted devices have a finite useful life span. Having consumed their power, or being fatigued by normal use and wear, they eventually require replacement. Of particular concern to medical practitioners are the electrodes associated with these devices. An electrode, being a physical device, also has a finite useful life span, and gradually loses its effectiveness because of fatigue caused by normal use and wear. For example, it is well known in the prior art that a muscle-to-electrode conduction interface will gradually deteriorate over time, thereby reducing or even eliminating the electrode's effectiveness. In U.S. Pat. Nos. 4,142,533, and 5,233,985, a cardiac pacemaker uses the interface resistance between the device electrode and the cardiac tissue to determine electrode condition. The resistance of the electrode-tissue interface is measured as a function of the electrode's impedance.

In another example, electrodes are often exposed to severe mechanical stress. These electrodes eventually fatigue. Their protective covering, and the center conductor, can fracture resulting in undesirable electrode performance. In particular, electrodes having multi-filament wire conductors fatigue whereby the filaments of the wire conductor fracture and protrude from the electrode. These protruding wire elements are undesirable and indicative of a defective electrode.

In U.S. Pat. Nos. 3,618,615, 3,830,242, and 4,527,567, the condition of a single electrode or a plurality of electrodes is determined by a cardiac pacemaker's response to low level externally emitted test signals. Only when the pacemaker fails to respond to the external signal are electrodes deemed to be of concern.

Another problem associated with implanted devices of the prior art is the inability to establish reliable communication between an implanted device and a location outside the patient's body. This problem is attributed to the severe attenuation of electromagnetic signals caused by the flesh and bones of the implant recipient. In U.S. Pat. No. 4,220,156, a cardiac pacemaker is equipped with an AM (amplitude modulated) receiver to detect control signals emitted from a source external to the patient's body.

To improve detectability, the AM signal in U.S. Pat. No. 4,220,156 is externally pulse modulated by the same source. However, the principal method used to achieve signal detection is to increase the amplitude of the external AM signal until the receiver of the implanted device can detect the modulated signal. The device disclosed in U.S. Pat. No. 4,220,156 is limited, however, to the gross considerations of the entire electrode interface condition.

In U.S. Pat. Nos. 4,281,664, an implanted device is equipped to transmit a damped sinusoidal frequency modulated signal to improve detection of the transmitted signal. And in U.S. Pat. No. 4,944,299, various forms of narrow band noise filtering, including digital signal processing and AM signal detection techniques, are employed to improve the reception and transmission of implant signals. Although these patents attempt to improve the communication problems associated with signal transmission through flesh and bone, they do not address the detection of localized electrode failures within the electrode itself.

For the foregoing reasons, there is a need for a device that can easily and accurately evaluate the condition of implanted electrodes or wire leads.

SUMMARY OF THE INVENTION

The present invention is directed to a device that can easily and accurately evaluate the condition of implanted electrodes or wire leads. In particular, this invention is useful for evaluating the condition of electrodes having wire conductors that fatigue whereby the filaments of the wire conductor fracture and protrude from the electrode. These protruding wire elements are undesirable and indicative of a defective electrode.

In accordance with one aspect of the present invention, a status monitoring system is provided for evaluating the condition of an electrode implanted in the body of a mammal. The system comprises a modulator for modulating interrogation signals on an electrode of an implanted device, and a monitor for analyzing modulated interrogation signals being reflected by the electrode.

The monitor comprises a transmitter for transmitting interrogation signals, a receiver for receiving and processing the signals reflected by the electrode, and a microprocessor for controlling the transmitter and the receiver. The microprocessor produces electrode condition data from the signals processed by the receiver.

In accordance with another aspect of the present invention, a communication system is provided for communicating the electrode condition data to a remote location. The communication system is in communication with the monitoring device. The interrogation signals are transmitted by the transmitter onto the electrode. The interrogation signals are modulated on the electrode by combining with a modulation signal generated by the modulator. The modulator is activated by the interrogation signals. The modulated interrogation signals are reflected by the electrode and received by the receiver. The receiver receives and processes the received signal into a form usable by the microprocessor, the microprocessor producing therefrom the electrode condition data.

In accordance with another aspect of the present invention an external monitoring device transmits an interrogation signal in the direction of an implanted device having an electrode. The implanted device having the electrode to be evaluated detects the interrogation signal and generates a modulation signal that is then applied to the electrode. The combined interrogation and modulation signal is then radiated by reflection from the electrode back in the direction of the monitoring device. The monitoring device receives, detects, and analyzes the reflected signal to determine the condition and structural integrity of the implanted electrode. By modulating the reflected signal, detection is greatly improved, thereby providing exceptional reliability and accuracy in evaluating the condition of the electrode.

In accordance with another aspect of the present invention, a remote modulation device is implanted near the medical device having an electrode in need of evaluation.

The remote modulation device generates a modulation signal whenever the external monitoring device transmits an interrogation signal. The interrogation and modulation signal combine and radiate by reflecting from the electrode back in the direction of the monitoring device. The monitoring device receives, detects, and analyzes the reflected signal to determine the condition and structural integrity of the implanted electrode. By modulating the reflected signal, detection is greatly improved, thereby providing exceptional reliability and accuracy in evaluating the condition of the electrode.

In accordance with another aspect of the invention, a remote modulation device is attached subcutaneously onto the lead of the medical device having an electrode in need of evaluation. The remote modulation device can easily be attached to the electrode by means of a one time small incision at a site near the electrode.

In accordance with another aspect of the invention, the external monitoring device is operable by any individual including the implant recipient. The monitoring device is held over the body near the implanted device. Once activated, the monitoring device quickly evaluates the implanted electrode and storing the information until need by a medical professional.

In all aspects of the invention, the status monitor interrogates the electrode of the implanted device with a signal that is generated and focused in the region of the electrode. Defective electrodes are detected by comparing the reflected signal of the electrode-under-test to a reference signal from a preferred electrode. The reflected signal from a defective electrode can be distinguished from non-defective electrodes by the presence of stub monopole resonances caused by stub-like elements protruding from the defective electrode. The frequency of the signal is varied in a range corresponding to potential stub monopole resonances associated with a range of protruding element lengths. The frequency of the signal can be varied as a function of time.

The signal transmitted by the monitor is reflected by the electrode. The signal is then received by the monitor and analyzed for the presence of stub monopole resonances. Due to the resonance effect of an excited stub monopole, an increase in amplitude of the reflected signal can be measured. The increase in amplitude is determined by comparing the reflected signal comprising resonances from one or more excited stub monopoles to the known reference electrode. In general, the reflected signal from a reference electrode, one without protrusions (monopole stubs), is characterized as having a flat or monotonic response.

Typically, an increase in amplitude can be measured at the resonance of the protruding section of a broken wire. For example, a quarter inch long monopole stub will be resonant at approximately 12 GHz in air and around 1.7 GHz in human tissue. As a result of this resonance, the reflected signal of a wire with a protruding section (monopole stub) will have an increased amplitude when compared to wire without protrusions It is an object of the present invention to provide an improved device for the evaluation of electrode condition. This and other features, aspects, and advantages of the present invention will become better understood with reference to the following descriptions, drawings, and appended claims.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE PREFERRED EMBODIMENT

Figure 1:
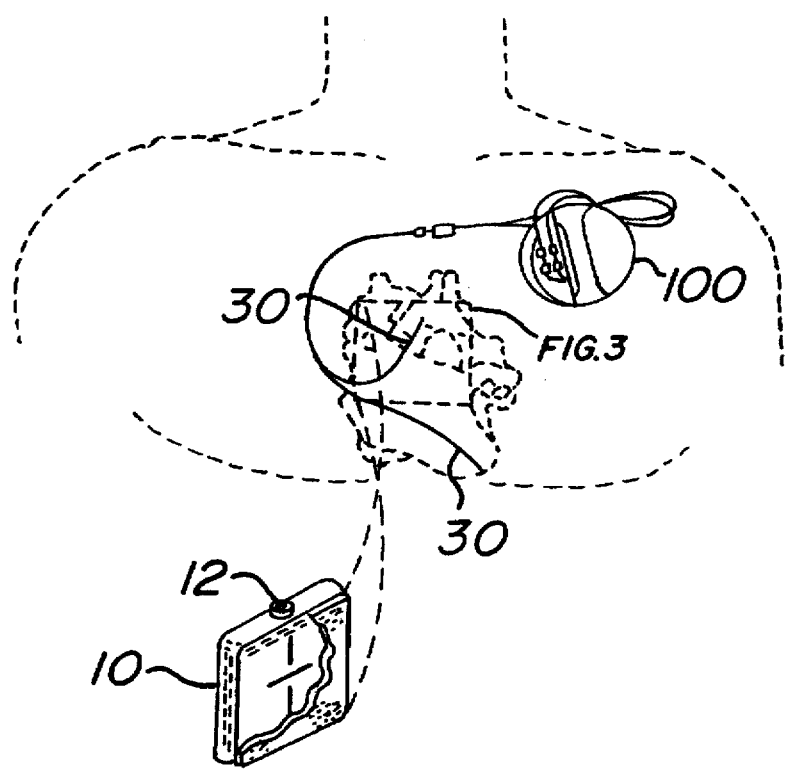
FIG. 1 shows an illustration of a preferred embodiment of a status monitor for anomaly detection in accordance with the present invention.

Referring to the drawings in detail, wherein like numerals indicate like elements, FIG. 1 shows a status monitor 10 in accordance with the present invention. The status monitor 10 is placed against a body of a mammal having an implanted device therein and having an electrode 30. The operator activates the device with the touch of a switch 12. The device transmits an interrogation signal which is received by the implanted device 100, causing a modulation signal to be generated on the implanted electrode 30.

Figure 2:
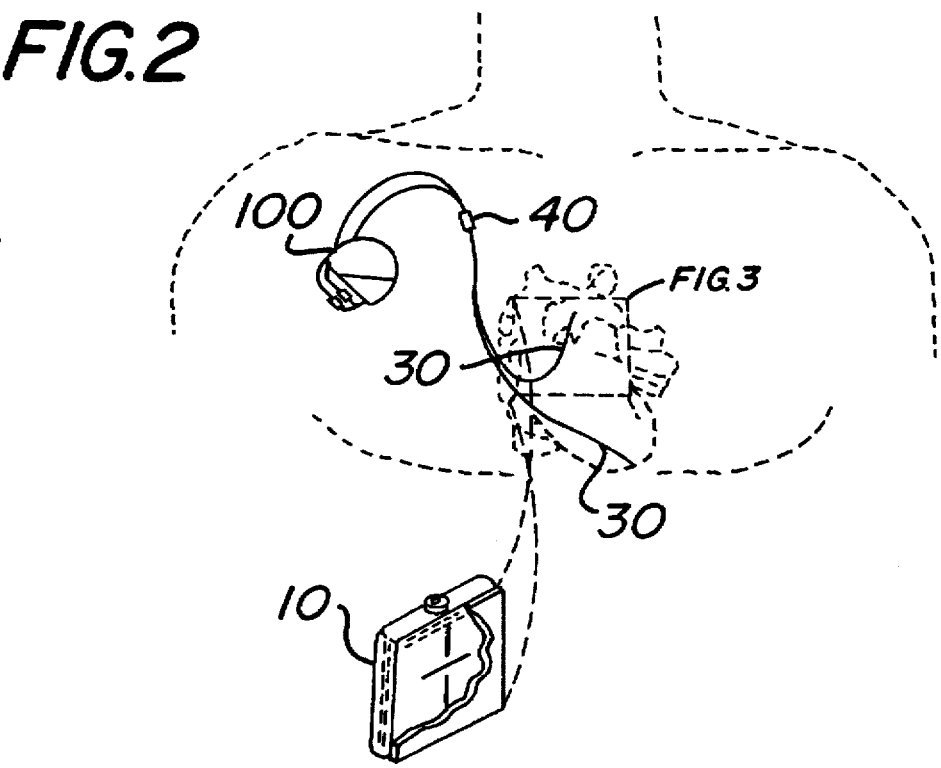
FIG. 2 shows an illustration of a preferred embodiment of a status monitor showing a remote modulation device in accordance with the present invention.

In one embodiment of the present invention as shown in FIG. 1, the modulation device 40 is incorporated into the implanted device 100. In another embodiment of the present invention, as shown in FIG. 2, the modulation device 40 is attached subcutaneously onto the electrode 30 of the implanted device 100. The modulation device 40 can easily be attached to the electrode 30 by means of a one time small incision at a site near the electrode 30, or can be incorporated when device 100 is originally implanted.

Figure 3:
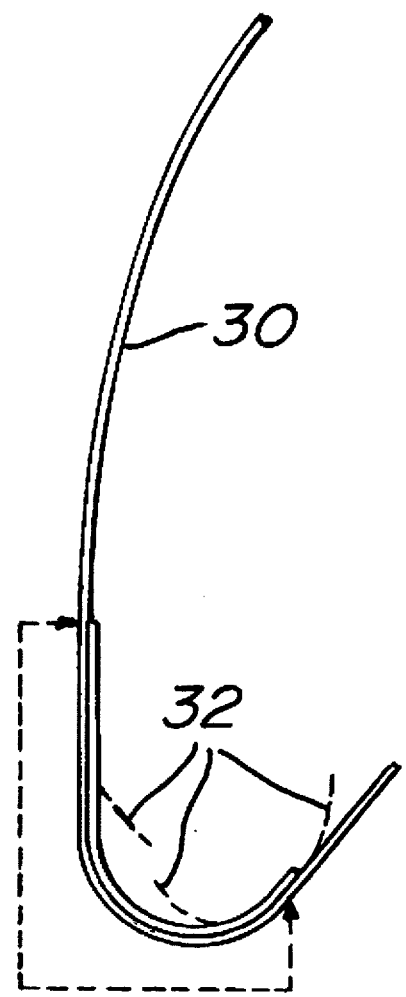
FIG. 3 shows an illustration of a typical implanted electrode.

The status monitor 10 interrogates the electrode 30 of the implanted device with a microwave signal that is generated and focused in the region of the electrode 30. The electrode 30 receives and reflects the signal. Defective electrodes as shown in FIG. 3, have small protruding wire elements 32. The protruding wire elements 32 interact with the signal thereby producing stub monopole resonances. The stub monopole resonances formed by the protruding wire elements 32 are indicative of a defective electrode. To enhance stub resonance detection, the frequency of the radiated signal is varied as a function of time, in a range of frequencies corresponding to potential stub monopole resonances. These stub resonances are excited by the transmitted signal and detected by the monitor 10.

The microwave signal transmitted by the monitor 10 is reflected by the electrode 30. The signal is then received by the monitor 10 and analyzed for the presence of stub monopole resonances. Due to the resonance effect of an excited stub monopole, an increase in amplitude of the reflected signal can be measured. The increase in amplitude is determined by comparing the reflected signal of a known reference electrode to that of the defective electrode exhibiting the measurable effect of resonance from an excited stub monopole. In general, the reflected signal from a reference electrode, one without protrusions (monopole stubs), is characterized as having a flat or monotonic response.

Typically, an increase in amplitude can be measured at the resonance of the protruding section of a broken wire. For example, a quarter inch long monopole stub will be resonant at approximately 12 GHz in air and around 1.7 GHz in human tissue. As a result of this resonance, the reflected signal of a wire with a protruded section (monopole stub) will have an increased amplitude when compared to wire without protrusions.

The system of the present invention further comprises a means to improve the signal to noise ratio (SNR) of the detectable signal reflected by the electrode 30. In one embodiment of the present invention, signal to noise ratio (SNR) of the detected reflected signal can be increased to a desired level by placing the detector on the patient's body in close proximity to the implanted electrode and by controlling the detection bandwidth. However, a direct reflection measurement, as described here, will result in poor signal quality due to the high clutter content of the reflected signal caused by high reflection background noise generated by the human body.

Specifically, clutter is that portion of the signal contributed by unwanted reflected energy from all undesired targets. In this application, unwanted reflected energy is produced by undesired targets such as bone, tissue, or other implanted devices. The amount of clutter present in the reflected signal is expressed as a ratio of signal to clutter.

To improve the signal to clutter ratio (SCR) of the measured reflected signal, polarimetric detection techniques such as: polarization discrimination and modulation/coherent detection are used. These polarimetric detection techniques are well known in the art and therefore need not be described in detail herein. Since the protruding wire elements 32 tend to protrude at an angle from the electrode 30, a reflection polarization component perpendicular to the electrode is generated. A polarimetric measurement is used to detect these variations in reflection polarization in quadrature. This polarization discrimination technique will improve the signal generated by the protruding wire elements 32 with respect to the signal generated by the electrode 30.

Figure 4:
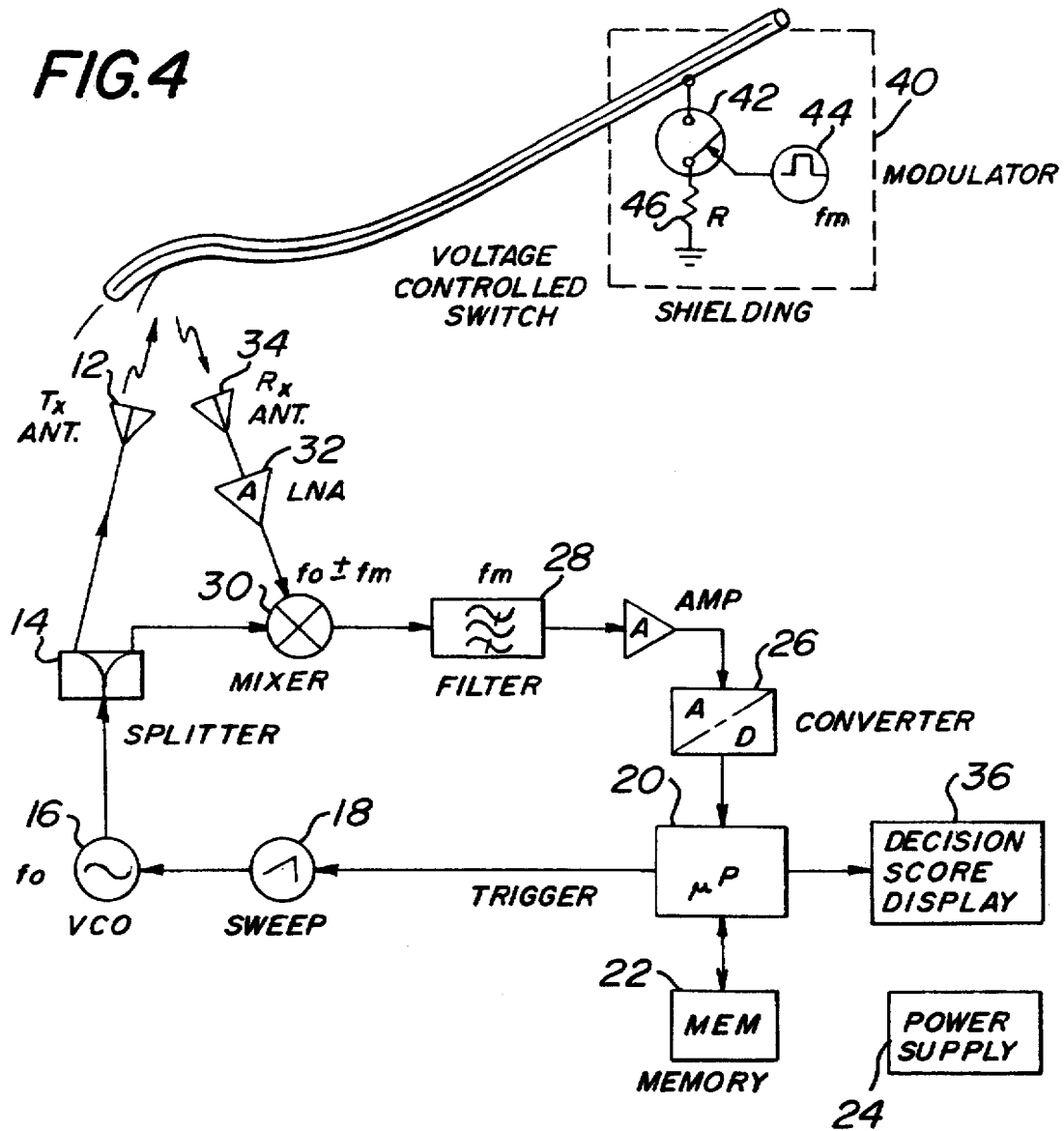
FIG. 4 shows a block diagram of a preferred embodiment of a status monitor in accordance with the present invention.

The modulation/coherent detection technique is used to separate the signal generated by the protruding wire elements 32 from the electrode 30 and the background noise generated by the human body. This is accomplished, as shown in FIG. 4, by applying an appropriate sinusoidal modulation on the electrode 30 by a modulator device 40. As an example, a sinusoidal modulation in the range between 30 KHz and 3 MHz can be applied. However, it is to be understood that this technique can be applied at any modulation frequency capable of being transmitted through a mammal's body.

A coherent detection scheme, established at a predetermined frequency, is then used to exclude all signals except for the reflected and modulated signal detected at the particular a predetermined frequency. By modulating the reflected signal, a desirable frequency offset of the original frequency of transmitted wave occurs. The frequency offset is then exploited so that the detection operation can be achieved at the low phase noise region of an oscillator.

Referring to FIG. 4, the polarimetric detection of the protruding wire elements 32 from the electrode 30 and the background noise generated by the human body is recorded and monitored for variation in periodic self-checks by the patient. When a protruding wire elements 32 is detected and analyzed by the monitor 10, it responds with an alarm to warn the patient.

In another embodiment of the present invention, the monitor 10, with the aid of either an internal or external telemetry or cellular device, transmits, by modem, cellular, or land telephone network, the data generated by the monitor for further analysis by medical professionals.

The present invention may be embodied in other specific forms without departing from the spirit or essential attributes thereof and, accordingly, reference should be made to the appended claims, rather than to the foregoing specification, as indicating the scope of the invention.

What is claimed is:

1. A status monitoring system for evaluating the condition of an electrode implanted in the body of a mammal, comprising:

(a) a modulator for modulating interrogation signals on an electrode of an implanted device;

(b) a monitor for analyzing modulated interrogation signals being reflected by the electrode, said monitor comprising:

a transmitter for transmitting interrogation signals, a receiver for receiving and processing said signals reflected by the electrode, a microprocessor for controlling the transmitter and the receiver, said microprocessor producing electrode condition data by comparing known electrode characteristics with said interrogation signal and said received signals processed by the receiver thereby producing electrode condition data; and (c) a communication system for communicating said electrode condition data to a remote location, said communication system being in communication with said monitor, said interrogation signals being transmitted by the transmitter onto the electrode the interrogation signals being modulated on the electrode by combining with a modulation signal generated by the modulator, the modulator being activated by the interrogation signals, said modulated interrogation signals being reflected by the electrode and received by the receiver, said receiver receiving and processing the received signal into a form usable by the microprocessor, said microprocessor producing therefrom said electrode condition data.

2. The status monitoring system of claim 1, wherein the microprocessor generates a transmitter triggering signal to a sweeping function generator, the function generator drives a voltage controlled oscillator, and the oscillator generates frequency sweeping radio frequency interrogation signals, said interrogation signals being transmitted by a transmitting antenna.

3. The status monitoring system of claim 2, wherein the receiver comprises a receiving antenna, a first amplifier and a homodyne frequency mixer, said mixer having a first input from the amplifier, a second input from the transmitter, the signal is coherently detected, filtered, amplified by a second amplifier and converted into a digital signal by a analog to digital signal convertor, said mixer and filter being matched to the modulation signal of the modulator, said digital signal being provided to the microprocessor.

4. The status monitoring system of claim 3, wherein the microprocessor generates the transmitter triggering signal in response to received signals.

5. The status monitoring system of claim 4, wherein the transmitter and the receiver have a frequency range of operation between 200 MHz and 2 GHz.

6. The status monitoring system of claim 1, wherein the modulator comprises a function generator for generating a modulation signal on the electrode, an electrically actuatable switch for connecting the modulator to the electrode when the switch is in the closed position, and a receiver for detecting the interrogation signals and for closing the electrically actuatable switch when the interrogation signal is detected.

7. The status monitoring system of claim 1, wherein the modulation device is incorporated into an implanted device having an electrode.

8. The status monitoring system of claim 1, wherein the modulation device is attached to the electrode of an implanted device.

9. A status monitoring system for evaluating the condition of electrodes implanted in the body of a mammal, comprising:

a modulation device for generating a modulation signal on an electrode, said modulation device being in communication with the electrode, a transmitter for generating an interrogation signal, a receiver for receiving a reflected signal, a microprocessor for controlling the transmitter and the receiver, said microprocessor for comparing known electrode characteristics with said interrogation signal and said received reflected signal thereby producing electrode condition data, and a communication system for transmitting said electrode condition data to a remote location, said communication system being in communication with said microprocesor, said transmitter generating the interrogation signal on the electrode, the interrogation signal activating the modulation device to generate the modulation signal on the electrode, the modulation signal and the interrogation signal combining and reflecting from the electrode, the reflected signal being received by the receiver, said receiver processing the signal into a form usable by the microprocessor, said microprocessor producing electrode condition data.

10. A status monitoring system for evaluating electrodes of implanted devices, comprising:

(a) a modulation device integral to the implanted device for generating a modulation signal on an electrode of an implanted device;

(b) a monitoring device placed in proximity to a body with an implanted device having an electrode, said monitoring device comprising, a microwave transmitter for generating a microwave interrogation signal, said interrogation signal activating the modulation device to generate the modulation signal on the electrode of the implanted device, said interrogation signal combining with said modulation signal on the electrode to produce a modulated interrogation signal, said modulated interrogation signal being reflected by the electrode of the implanted device, a receiver for detecting and processing the reflected modulated interrogation signal, a microprocessor in communication with the receiver, for analyzing the reflected signal thereby and producing electrode analysis and data; and a communication system for communicating said electrode analysis and data to a remote location.

11. A method for evaluating the condition of electrodes implanted in the body of a mammal, comprising the steps:

(a) generating a modulation signal on an electrode of an implanted device;

(b) transmitting an interrogation signal to the implanted electrode such that the interrogation signal combines with said modulation signal on the electrode to produce a modulated interrogation signal, said modulated interrogation signal being reflected by the electrode of the implanted device, (c) receiving the reflected modulated interrogation signal, (d) comparing known electrode characteristics with said interrogation signal and said received signal thereby producing electrode condition data, and (e) communicating said electrode condition data to a remote location.

* * * * *